(12) United States Patent
Schmidt

(10) Patent No.: US 11,850,451 B2
(45) Date of Patent: Dec. 26, 2023

(54) COSMETIC COMPOSITIONS AND METHODS FOR IMPROVING SKIN CONDITIONS

(71) Applicant: Lucolas-M.D. Ltd., Birmingham (GB)

(72) Inventor: Alfred Schmidt, Nambsheim (FR)

(73) Assignee: Lucolas-M.D. Ltd., Birmingham (GB)

(*) Notice: Subject to any disclaimer, the term of this patent is extended or adjusted under 35 U.S.C. 154(b) by 293 days.

(21) Appl. No.: 16/984,721

(22) Filed: Aug. 4, 2020

(65) Prior Publication Data

US 2020/0360734 A1 Nov. 19, 2020

Related U.S. Application Data

(63) Continuation-in-part of application No. 16/710,517, filed on Dec. 11, 2019, now abandoned, which is a continuation of application No. 13/982,539, filed as application No. PCT/EP2012/051421 on Jan. 30, 2012, now abandoned.

(60) Provisional application No. 61/444,795, filed on Feb. 21, 2011.

(30) Foreign Application Priority Data

Jan. 31, 2011 (DE) .................. 10 2011 003 408.0

(51) Int. Cl.

| | | |
|---|---|---|
| *A61Q 19/00* | (2006.01) | |
| *A61K 8/49* | (2006.01) | |
| *A61K 8/73* | (2006.01) | |
| *A61Q 19/08* | (2006.01) | |
| *A61Q 19/06* | (2006.01) | |
| *A61K 8/63* | (2006.01) | |
| *A61K 8/9789* | (2017.01) | |
| *A61K 8/97* | (2017.01) | |

(52) U.S. Cl.
CPC .............. *A61Q 19/00* (2013.01); *A61K 8/49* (2013.01); *A61K 8/4986* (2013.01); *A61K 8/63* (2013.01); *A61K 8/735* (2013.01); *A61K 8/97* (2013.01); *A61K 8/9789* (2017.08); *A61Q 19/06* (2013.01); *A61Q 19/08* (2013.01)

(58) Field of Classification Search
CPC ........ A61Q 19/00; A61Q 19/06; A61Q 19/08; A61K 8/4986; A61K 8/49; A61K 8/735; A61K 8/97; A61K 8/9789

See application file for complete search history.

(56) References Cited

U.S. PATENT DOCUMENTS

| | | | |
|---|---|---|---|
| 5,709,868 A * | 1/1998 | Perricone ............... | A61K 31/19 424/59 |
| 5,945,109 A | 8/1999 | Schmidt et al. | |
| 7,238,377 B2 | 7/2007 | Piccirilli et al. | |
| 8,343,948 B2 | 1/2013 | Schmidt et al. | |
| 2005/0118282 A1 * | 6/2005 | Castor .................. | A61K 36/889 514/169 |
| 2005/0266064 A1 * | 12/2005 | McCarthy .............. | A61K 8/676 514/474 |
| 2006/0003033 A1 | 1/2006 | McClellan et al. | |
| 2006/0165644 A1 | 7/2006 | Tanaka et al. | |
| 2007/0148123 A1 | 6/2007 | Wieland et al. | |
| 2010/0255127 A1 | 10/2010 | Norimoto et al. | |
| 2010/0256102 A1 | 10/2010 | Windisch | |
| 2011/0117218 A1 | 5/2011 | Schmidt | |

FOREIGN PATENT DOCUMENTS

| | | |
|---|---|---|
| CA | 2 324 077 | 9/1999 |
| DE | 10 2008 012 988 | 10/2009 |
| DE | 102008034265 A * | 1/2010 |
| DE | 102008034265 A1 | 1/2010 |
| EP | 0 943 333 | 9/1999 |
| EP | 1265583 | 9/2001 |
| JP | H09188607 A | 7/1997 |
| JP | 2001500841 A | 1/2001 |
| JP | 2002-316916 A | 10/2002 |
| JP | 2003-306415 A | 10/2003 |
| JP | 2004-502634 A | 1/2004 |
| JP | 2006-028045 A | 2/2006 |
| JP | 2006306819 A | 11/2006 |
| JP | 2007056219 A | 3/2007 |
| JP | 2008-537960 A | 10/2008 |
| JP | 2008-303202 A | 12/2008 |
| JP | 2009138028 A | 6/2009 |
| JP | 5255245 B2 | 8/2013 |
| RU | 2078561 C1 | 5/1997 |
| RU | 2295951 C1 | 3/2007 |
| WO | 97/36570 | 10/1997 |
| WO | 2004016236 A1 | 2/2004 |
| WO | 2006/113505 A2 | 10/2006 |
| WO | 2009/066712 A1 | 5/2009 |
| WO | 2009109402 A2 | 9/2009 |

OTHER PUBLICATIONS

Okolo et al., Afr J Tradit Complement Altern Med, 2016, 13(4):132-144. (Year: 2016).*

The printout of Wikipedia—Green tea, downloaded on Jun. 16, 2023 from the website: https://en.wikipedia.org/wiki/Green_tea (Year: 2023).*

Santern et al., "History of Aromatase: Saga of an Important biological Mediator and Therapeutic target", Endocrine Reviews, Jun. 2009, 30(4): 343-375.

Thompson et al., "Utilization of Oxygen and Reduced Nicotinamide Adenine Dinucleotide Phosphate by Human Placental Microsomes during Aromatization of Androstenedione*", The Journal of Biological Chemistry, vol. 249, No. 17, Sep. 10, 1974, pp. 5364-5372.

(Continued)

*Primary Examiner* — Allison M Fox
*Assistant Examiner* — Qing Xu
(74) *Attorney, Agent, or Firm* — Locke Lord LLP; Nicholas J. DiCeglie, Jr.

(57) ABSTRACT

The invention relates to the use of an agent and a composition, respectively, comprising the following active ingredients:
a) an aromatase inhibitor and/or a 5-α-reductase inhibitor,
b) an antioxidant, and
c) hyaluronic acid for cosmetic purposes.

13 Claims, No Drawings

(56) References Cited

OTHER PUBLICATIONS

Lo Scalzo, "Measurement of Free Radical Scavenging Activity of Gallic Acid and Unusual Antioxidants as Sugars and Hydroxyacids", EJEAFChe, 9(8), 2010, pp. 1360-1371.

Yamaguchi et al., "HPLC Method for Evaluation of the Free Radical-scavenging Activity of Foods by Using 1,1-Diphenyl-2-picrylhydrazyl#", Biosc. Biotechnol. Biochem., 62 (6), 1201-1204, 1998.

"Skin Recorvery Moisturizer", MCK Laboratories, Data, Mintel, GNPD, Feb. 2009.

http://www.ayushveda.com/dietfitness/how-does-alpha-lipoic-fight-cellulite/.

Russion Office Action, and English translation thereof, dated Mar. 24, 2016, issued during the prosecution of corresponding Russian Patent Application No. 2013140385.

Official Action, issued in corresponding Russian Patent Application No. 2013140385, dated Jul. 8, 2016.

Cited website: http://www.dom-olhon.ru/news/412 with electronic translation.

Patent Examination Report No. 2, issued in corresponding Australian Patent Application No. AU 2012213590, dated Aug. 24, 2016.

K. Satoh et al., "Inhibition of aromatase activity by green tea extract catechins and their endocrinological effects of oral administration in rats," Food and Chemical Toxicology 40, 925-933, (2002).

M. Kapiszewska et al., "High tea consumption diminishes salivary 17b-estradiol concentration in Polish women," British Journal of Nutrition 95, 989-995, (2006).

S. Liao et al., "Growth suppression of hamster flank organs by topical application of catechins, alizarin, curcumin, and myristolec acid," Arch Dermatol Res 293, 200-205, (2001).

S. Liao et al., "Selective Inhibition of Steroid 5a-Reductase Isozymes by Tea Epicatechin-3-Gallate and Epigallocatechin-3-Gallate," Biochemical and Biophysical Research Communications, vol. 214, No. 3, pp. 833-838, (1995).

Vengerovskiy, A.I., Bulletin of Siberia medicine, 3, 2003, pp. 49-56.

Harkevich, D.A., Pharmacology: Manual, GEOTAR-Media, 2006, pp. 66-71.

Office Action issued by the Russian Patent Office dated Jan. 25, 2017, in corresponding Russian Patent Application No. 2013140385/15 (061458).

Notice of Reasons for Rejection (Office Action) issued in corresponding Japanese Patent Application No. JP 2016-204836, dated Oct. 31, 2017.

Notice of Reasons for Rejection (Office Action) issued in corresponding Japanese Patent Application No. JP 2016-15583, dated Dec. 20, 2017.

\* cited by examiner

COSMETIC COMPOSITIONS AND METHODS FOR IMPROVING SKIN CONDITIONS

CROSS REFERENCE TO RELATED APPLICATIONS

This application is a continuation-in-part of U.S. Ser. No. 16/710,517 filed on Dec. 11, 2019; which application is a continuation of U.S. Ser. No. 13/982,539 filed Jul. 30, 2013; which application is the national phase under 35 U.S.C. § 371 of PCT International Application No. PCT/EP2012/ 051421 which has an International filing date of Jan. 30, 2012, which claims priority to German Patent Application No. 10 2011 003 408.0, filed Jan. 31, 2011 and U.S. Provisional Application No. 61/444,795, filed Feb. 21, 2011. The contents of these applications are incorporated herein by reference in their entirety.

FIELD OF INVENTION

The invention relates to the cosmetic use of a composition for improving the general condition and appearance of the skin.

BACKGROUND OF INVENTION

Depending on the respective cultural environment or the respective epoch, the ideals of beauty are subject to certain transformations. Nevertheless, also today a flawless appearance is of great importance for the majority of the population. In this respect, the condition and the appearance of the skin play a decisive role.

The skin represents a very versatile organ, having a series of essential functions in the human or animal organism, respectively. For instance, on the other hand, the skin provides a barrier, which delimits the body externally and protects it from harmful environmental influences or allows for the exchange with the environment, respectively. On the other hand, the skin has important metabolic functions and is involved, for example, in a significant manner in the defense of pathogens, but also in allergic reactions.

As a consequence of e.g. nicotine and/or alcohol abuse and of the permanent exposition of the skin to influences from the environment such as, for example, UV-radiation, the so-called exogenic skin aging occurs. Moreover, endogenous factors such as the genetic predisposition, additionally cause an aging effect.

One consequence of skin aging is the development of wrinkles due to drying and loss of elasticity in the epidermis. This is accompanied by impaired wound healing and an overall thinner epidermal layer. This causes a stronger visibility of modified blood vessels, in particular in the case of spider veins. A further condition significantly compromising the appearance of the skin is cellulite. Cellulite is not a condition caused by a disease but rather an aesthetic problem, which occurs mostly in women. Therein, the deposition of fat in the subcutis is increased leading, in cases of connective tissue-weakness, to irregular dents on the skin, the so-called orange skin. Also the so-called stretch marks represent an impairment of life quality for many people. Stretch marks are formed by overstretching of the connective tissue in the subcutis, e.g. due to strong weight increase. The overstretching of the connective tissue first leads to blue-reddish stripes; due to the scarring of these tissue ruptures they appear as bright stripes later on, which are distinct from the surrounding skin to a varying degree depending on the pigmentation of the affected skin area.

The cosmetic industry offers various options aiming at counteracting signs of aging in general. The success of the respective products and methods in the long term, however, does often not come up to the expectations of the user. For instance, mainly two methods are used in order to remove spider veins, both of which are connected to side-effects and in both of which frequent relapses occur. Sclerotherapy is an invasive method, in which, besides pain, side-effects such as hematomas and venous thromboses can occur. In laser treatment, which frequently requires multiple sessions, allergic skin reactions and pain can occur as side effects. Recurrence rates are relatively high in both methods.

There is therefore a need for cosmetic uses, which counteract the phenomena mentioned above and signs of skin aging in general.

SUMMARY OF THE INVENTION

It is an object of the present invention to provide a cosmetic use of a composition for improving the appearance of the skin. In particular, the visible consequences of cellulite, stretch marks, spider veins and signs of aging in general shall be reduced or avoided.

This objective is solved by the present invention as defined in claim 1. Embodiments are defined in the respective sub-claims.

DETAILED DESCRIPTION OF THE INVENTION

The present invention relates to the use of an agent or a substance, in particular of a composition, which comprises the following active ingredients:
a) an aromatase inhibitor and/or a 5-α-reductase inhibitor,
b) an antioxidant and
c) hyarolonic acid
for cosmetic purposes.

In a preferred embodiment, the composition of the present invention comprises
a) an aromatase inhibitor and a 5-α-reductase inhibitor,
b) an antioxidant and
c) hyaluronic acid
for cosmetic purposes.

In the use according to the invention the single components a), b) and/or c) can each be used independently from each other together, i.e. in a common composition, or alternatively separately in separated forms, in the latter case however, in such a manner that at least they are applied during the same period of time. The use in a common composition is preferred.

The skin condition is substantially influenced by the microcirculation in the skin. The latter is obstructed, for example, by the size increase or multiplication of fat cells, respectively. The increase of fat cells or the fat contents in the cells, respectively, reduces the skin's capacity to bind water and leads to the formation of wrinkles.

In the context of the present invention, it has surprisingly been found that the use of the composition according to the invention, which besides an aromatase inhibitor and/or a 5-α-reductase inhibitor, preferably besides an aromatase inhibitor and a 5-α-reductase inhibitor, can also comprise an antioxidant and hyaluronic acid, substantially improves the appearance of the skin. The use according to the invention does not only lead to the reduction of wrinkles, but also to an improvement of cellulite, stretch marks, spider veins as well as of the general appearance of the skin surface. In particular, signs of aging (e.g. age spots, eye wrinkles, general wrinkles in the face, etc.), aging of the décolleté or signs of UV-aging (photo aging) are improved by the use according to the invention.

Without wishing to limit the scope of the present invention by a theory, it is assumed that the effect according to the invention is based on the improvement of the microcirculation in the skin. This does not only lead to increased water-binding in the skin, but also to a strengthening of the collagen fibers and thus to a smooth skin surface. Furthermore, the microcirculation improved by the use according to the invention, apparently also enhances metabolic processes in the skin. It is presumed that harmful metabolic products, which in the case of insufficient microcirculation accumulate in the skin, are metabolized and/or removed via the lymph.

Thereby, in addition to the hormonal balance, also the metabolic equilibrium of the skin is re-established and the connective tissue is strengthened. It is assumed that simultaneously the effect of harmful radicals is reduced or totally avoided by the effect of the anti-oxidant providing better protection of the skin against new damages. By this approach, which aims at eliminating the central causes of the majority of skin damages, the most diverse phenomena can thus be treated that have a negative impact on the skin's appearance. The skin's general condition is improved by an improved supply of the skin and an improved protection of the skin against damages caused by radicals and dehydration. It is further assumed that the unexpected improvement of the skin's appearance is caused by a synergistic cooperation of the single components of the composition according to the invention. The conversion of testosterone to estrogen is locally reduced or blocked by the effect of the aromatase inhibitor and/or the 5-α-reductase inhibitor, respectively. This leads, amongst other effects, to a reduced increase of fat cells and/or to a decrease of the volume/fat content of fat cells, respectively. At the same time, anabolic processes are enhanced, which contribute to the tightening of connective tissue and to wound healing. In particular, the simultaneous use of hyaluronic acid is important since it additionally enhances the effect of the aromatase inhibitor and of the 5-α-reductase inhibitor, respectively, by improving the absorption of these active ingredients and that of the antioxidant and by retaining the active ingredients in the skin.

As mentioned above, the antioxidant protects against free radicals and thus reduces or blocks a new damage of the skin. Apparently, the effects of the single active ingredients amplify each other therein in a disproportionate manner, which leads to the unexpected improvement of the skin's general condition.

The invention shall be illustrated in detail by the following description of preferred embodiments, without, however, limiting the general concept according to the invention.

The present invention relates to the use of an agent or a composition, respectively, which, besides an aromatase inhibitor and/or a 5-α-reductase inhibitor, also contains an antioxidant and hyaluronic acid, for cosmetic purposes. In a preferred embodiment, the composition contains both, an aromatase inhibitor and 5-α-reductase-inhibitor, and additionally an antioxidant and hyaluronic acid.

In the meaning of the present invention, the use of an antioxidant in combination with an aromatase inhibitor and/or a 5-α-reductase inhibitor, preferably an aromatase inhibitor and a 5-α-reductase inhibitor, and the further component hyaluronic acid, counteracts the aging process of the skin and improves—mainly due to the combination with hyaluronic acid—the microcirculation in the skin.

Aromatase inhibitors in the meaning of the present invention are all substances, which—independently from their structure—are characterized by the common feature that they effectively inhibit or even inactivate aromatase (review article: Santen et al., Endocrine Reviews 2009; 30:343-375). The capacity of substance to inhibit or inactivate, respectively, aromatase, can be determined by methods known to the skilled person. A radiometric assay allows for measurement of aromatase activity in just one step via determination of tritium-release from a tritium-labeled substrate (Thompson and Siiteri, Journal of Biological Chemistry 1974; 249:5364-5372). The group of aromatase inhibitors is structurally heterogenous and comprises steroidal as well as non-steroidal compounds, wherein representatives of both groups are relevant for the medication in the meaning of the invention. As non-steroidal aromatase inhibitors, e.g. Anastrazol, Letrozol and Vorozol can be used. Possible steroidal aromatase inhibitors (aromatase-inactivators) are 4-hydroxyandrostenedione, Exemestane, 4-acetoxyandrostenedione, 5-α-androst-3-ene-17-one and 3-α, 4-α-epoxy-5-α-androstane-17-one. It is also possible that, as a steroidal aromatase-inhibitor (inactivator), extracts of plant(s) or of part(s) of plant(s) that exhibit aromatase inhibiting (inactivating) function are present in the composition of the present invention. Such extracts are for example an extract of soya beans (*Glycine soya*), or an extract of rapeseed (*Brassica campestris*). It is particularly preferred to use an exract of rapeseed as steroidal aromatase inhibitor (inactivator). It has been surprisingly found that the use of plant extract(s), and in particular the use of a *brassica campestris* extract, can result in a particular improved general condition of the skin. As such, in certain embodiments, the steroidal aromatase inhibitor is a plant-based extract.

In certain embodiments, the steroidal aromatase inhibitor is not a chemically or artificially synthesized steroidal aromatase inhibitor. In particular embodiments, the steroidal aromatase inhibitor is not one or more steroidal aromatase inhibitors selected from the group consisting of 4-hydroxyandrostenedione, Exemestane, 4-acetoxyandrostenedione, 5-α-androst-3-ene-17-one and 3-α, 4-α-epoxy-5-α-androstane-17-one.

5-α-reductase inhibitors in the meaning of the present invention are all substances, which reduce or completely inhibit the activity of 5-α-reductase type I and/or type II. Examples of 5-α-reductase inhibitors, which can be used according to the invention, are, amongst others, the extract from the fruits of saw palmetto (*Serenoa repens*, syn. *Sabal serrulata*), roots of stinging nettle (*Urtica dioica*), bark extract of African plum (*Pygeum africanium*), extract from pumpkin seeds (*Cucurbita pepo* seed) or Finasteride.

In certain embodiments, the 5-α-reductase inhibitors is not Finasteride.

In certain embodiments, the 5-α-reductase inhibitor, the steroidal aromatase inhibitor, and optionally the antioxidant are plant-based extracts. This plant-based extracts are disclosed elsewhere herein.

According to the present invention, the aromatase is preferably of an effectiveness, which is characterized by an average inhibitory concentration IC(50) of from 0.2 nM to 500 nM.

The 5-α-reductase inhibitor in the meaning of the invention is preferably characterized by an average inhibitory concentration IC(50) from 5 nM to 500 nM.

An antioxidant according to the present invention is a "radical scavenger", which captures free radicals or terminates their detrimental influence on the cell. The antioxidant's substance should differ from the aromatase inhibitor.

While the antioxidants' mechanism of action is of the same direction and consistent in the meaning of the invention, the group of antioxidants is structurally very heterogenous. Suitable substances in the meaning of the invention are selected according to their capacity to prevent the oxidation of other molecules. The skilled person is capable of identifying an antioxidant by established and published methods. The processes are known to a skilled person and shall not be explained here in detail. Thus, e.g. the amount of free radicals can be measured by EPR (electric paramagnetic resonance; Lo Scalzo, EJEAFChe 2010; 9:1360-1371). Therefore, substances such as 5,5-dimethyl-1-pyrrolin-N-oxide (DMPO) or 1,1-diphenyl-2-picrylhydrazyl (DPPH) are used, which have a high affinity to free radicals and together with these form stable compounds that can be measured spectrometrically. Processes are also used, in which the substance to be measured is purified chromatographically (e.g. via HPLC; Yamaguchi et al., Bioscience, Biotechnology, and Biochemistry 1998; 62:1201-1204). In the meaning of the present invention, antioxidative substances are used. The used antioxidants can be substances of various chemical classes and different origin. These can also be antioxidant substances, which occur in the organism, which amount and availability, respectively, are effectively increased, however, by the additional administration in the context of the use according to the invention, and/or which are eventually provided just at the desired target site by suitable application. Non-enzymatic antioxidants comprise, in particular, flavonoids (e.g. oligomeric proanthocyanidines (OPC), anthocyanes or polyphenoles such as quercetin or catechin); vitamins (e.g. vitamin C, vitamin E); carotenoids (e.g. β-carotin, lycopen, lutein); minerals (e.g. copper, manganese, zinc, selenium); hormones (e.g. melatonin); steroids (e.g. cortisol); ubiquinones; N-acetylcysteine; α-lipoic acid; and an extract of green tea containing an antioxidative effective composition of polyphenols, optionally also amino acids, mineral nutrients (trace elements) and polysaccharides, in particular which contains the specific highly antioxidative acting polyophenols epicatechin and epigallocatechin (e.g. OM24®, obtainable from Omnimedia, Switzerland); and glutathione. A further example of a suitable antioxidant is a plant-based extract, e.g. an extract of camellia sinensis. Some enzymes fulfill the function of antioxidants and are called enzymatic anti-oxidants such as e.g. glutathione peroxidase, superoxide dismutase and katalase.

All the extracts that are suitable for being used in the present invention are extracts that are highly enriched with regard to the respectively desired activity or function. For example, if it is desired to have an extract that exhibits aromatase-inhibiting (inactivating) function, extract fractions are selectively isolated that exhibit said desired function. The selective isolation of extract fractions having aromatase and/or 5α reductase inhibiting function can be verified by appropriate testing of the fractions for the respective inhibitory effect and can be collected accordingly, wherein in each case known specific inhibition assays can be used.

In general, the extract can be obtained from the whole plant or a part thereof, e.g. from leaves, stems or branches, from the bark, flowers, fruits, roots or the like. Preferably, prior to the extraction, the plant source is grinded, crushed or pulverized. Further optional processing steps are heating, refluxing, filtration, concentration, spray drying, freeze-drying. Preferably, a specific isolation step separating the extracted sample e.g. by using appropriate chromatographic methods, and isolating the respective fractions with the desired effect and, as the case may be, further purifying, is added. By doing so, for instance the isolation of the target can take place by determining and verification of the respective desired activity, and/or by testing for a substantial content of flavanoids and/or preferably of phytosterols, in particular of beta-sitosterol, stigmasterol and campesterol.

Particularly preferred, the plant extract exhibiting 5-alpha reductase inhibiting activity/function and/or aromatase-inhibiting (inactivating) activity/function represents an extract being rich in phytosterols and/or flavanoids, i.e. the proportion of phytosterols and/or flavanoids based on the total plant extract of the 5-α-reductase inhibitor or the aromatase-inhibitor is e.g. at least 50% by weight, further preferred at least 75% by weight, further preferred at least 90% by weight, and particularly preferred at least 95% by weight, at least 97% by weight, or at least 99% by weight.

In order to predominantly isolate the preferred steroidal active ingredients from the mentioned plants (e.g. Brassica campestris, saw palmetto), they are preferably extracted with organic solvents, e.g. with methanol, ethanol, hexanol, glycol, such as ethylene glycol or 1,3-butyleneglycol, acetone, hexane, benzene, toluene, chloroform. A particularly preferred extracting agent is ethanol.

The specific extracts that are used in the composition of the present invention are highly specific and highly selective extracts which are in no way comparable to extracts occurring in nature (such as rapeseed oil or soybean oil, or serenoa serrulata fruit extract, wherein the extracts have been obtained with no specific enrichment process applied) or extracts produced in a traditional (conventional) way. For example, rapeseed oil essentially consists of oleic acid (51-70 wt.-%), linoleic acid (15-30 wt.-%) and linolenic acid (5-14 wt.-%), and further comprises lecithin. Additionally, vitamins are comprised, particularly vitamins E, K, and provitamin A.

The rapeseed (Brassica campestris) extract that can be used in the composition of the present invention is a highly enriched mixture of different sterols, namely β-sitosterol, β-sitosterol acetate, brassicasterol, brassicasterolacetate, camposterol, camposterol acetat, avenasterol, avenasterol acetate, stigmasterol, and stigmasterol acetate. The content of sterols in the plant extract that can be used in the composition of the present invention is more than 95% by weight, preferably more than 97% by weight, and even more preferably more than 99% by weight. In order to obtain such a highly enriched extract, phytosterols are extracted by applying a crystallisation process, the starting material (educt) of such crystallisation process can be rapeseed oil. Purification is carried out by filter processes and multiple recrystallization.

The thus-obtained extract can be in form of a powder that is insoluble in water.

An example of an extract of the present invention that exhibits 5-α-reductase inhibiting function is an extract from the fruit of saw palmetto.

Further examples are: extract from the root of stinging nettle, bark extract of African plum, extract from pumpkin seed.

The composition of an extract can be determined via HPLC, gas chromatography (GC) or GCMS.

In a particularly preferred embodiment, the extract that is present in the composition of the present invention consists of at least 95 wt.-%, preferably at least 99% wt.-% phytosterols.

The selective isolation of extract fractions having aromatase and/or 5α reductase inhibiting function can be verified by appropriate testing of the fractions for the respective inhibitory effect and can be collected accordingly, wherein in each case known specific inhibition assays can be used.

Hence, all extracts that are contained in the composition of the present invention are standardised in relation to the respectively desired activity/function: aromatase-inhibition and 5-α-reductase inhibition. Standardisation can be carried out for example by applying an aromatase-inhibition assay or a 5-α-reductase-inhibition assay.

In comparison with possibly only endogenously occurring, or if so only randomly or for other purposes added antioxidants, according to the invention it can be ensured by adjusting appropriate amounts or by topical application that a desired cosmetic effect is achieved.

In a particular embodiment, the antioxidant, which is used in the cosmetic composition, is α-lipoic acid (1,2-dithiolan-3-pentanoic acid) or green tea extract containing polyphenols, in particular OM24® (a tea plant extract of epigallocatechin having antioxidant properties which combines a blend of polyphenols, catechins and amino acids from tea plant leaves, obtainable from Omnimedia, Switzerland). α-lipoic acid is active in the aqueous as well as in the lipid phases of the cells. This is particularly the case in combination with hyaloronic acid. This allows for different possibilities of administration. α-lipoic acid is readily converted into dihydro-lipoic acid in the organism. Dihydro-lipoic acid regenerates other further antioxidants such as vitamin C and vitamin E, which can lead to further amplified effects in the administration of α-lipoic acid. α-lipoic acid furthermore induces the synthesis of glutathione in the tissue.

Moreover, α-lipoic acid regenerates glutathione from glutathione disulfide.

In the topical use of the composition on the skin the active ingredients are applied to the skin area to be treated. The amount of active ingredients therein is preferably selected in such a manner that no plasma levels but only locally effective concentrations are reached. As a consequence, undesired systemic effects can be avoided. In this manner, undesired side-effects can be avoided even in the use over a longer period.

Alternatively, other application forms can be used, such as e.g. spraying the active ingredients onto the skin areas to be treated.

Therein, the active ingredients can be applied separately from each other or in a common composition, as long as it is ensured that the active ingredients reach the target tissue at the same time or that the time intervals at least overlap, in which the single active ingredients are present in the target tissue as active substances.

In a preferred embodiment, the use according to the invention comprises α-lipoic acid and hyaluronic acid in combination with an aromatase inhibitor and a 5-α-reductase inhibitor. In a particularly preferred embodiment, the use according to the invention comprises α-lipoic acid or *camelia sinensis* extract as antioxidant, hyaluronic acid, 4-acetoxyandrostenedione or extract of *brassica campestris* as steroidal aromatase-inhibitor, and *serenoa serrulata* fruit extract as 5-α-reductase inhibitor. The use of green tea extract containing polyphenols, in particular OM24® (epigallocatechin obtainable from Omnimedia, Switzerland) as antioxidant instead of or in addition to the use of α-lipoic acid is also possible.

Other further excipients, which are commonly used in cosmetic compositions (creams, ointments, gels, foams, tinctures, lotions, etc.), can be combined with the active ingredients mentioned above. In particular, the composition according to the invention can comprise excipients, which are commonly used in topical application forms. Likewise, respective carriers and excipients can be used for the provision as a spray, that are known to the skilled person.

In the meaning of the present invention, the preferred concentrations of the aromatase inhibitor in the composition are in a range from 0.25 weight-% to 1.5 weight-% (e.g. in cellulite 0.6 weight-%).

Preferably, the concentrations of the aromatase inhibitor in the composition are in a range from 0.5 weight-% to 1.8 weight-%, or in a range from 0.8 weight-% to 1.6 weight-%, or in a range from 1.0 weight-% to 1.5 weight-%.

If the aromatase-inhibitor is a plant extract, e.g. a brassica campestris extract, the concentration of said extract in the composition is in a range from 1.0 weight-% to 1.8 weight-%, preferably in a range from 1.3 weight-% to 1.6 weight-%, more preferably about 1.5 weight-%.

According to the invention, the concentration of the 5-α-reductase inhibitor is in the range from 0.5 weight-% to 5 weight-%.

Preferably, the concentration of the 5-α-reductase inhibitor is in the range from 0.8 weight-% to 2.0 weight-%, or in a range from 0.8 weight-% to 1.6 weight-%, or in a range from 1.0 weight-% to 1.3 weight-%, more preferably about 1.2 weight-%, in particular if the 5-α-reductase inhibitor is a plant extract, e.g. a *serenoa serrulata* fruit extract.

If the 5-α-reductase inhibitor is *serenoa serrulata* fruit extract, it is further preferred that the concentration of the 5-α-reductase inhibitor is about 1.2 weight-%.

The antioxidant is preferably present in a concentration of from 0.2 weight-% to 2.5 weight-% in the composition, more preferably in a concentration of from 0.2 weight-% to 1.0 weight-%, or from 0.5 weight-% to 1.0 weight-%. For example, if the antioxidant is *camelia sinensis* extract, the preferred concentration is about 1.0 weight-%, and if the antioxidant is alpha lipoic acid, the concentration is about 0.5 weight-%.

Examples of the composition are as follows:

1.
1.5% *brassica campestris* extract (steroidal aromatase inactivator)
1.2% *serenoa serrulata* fruit extract (5-α-reductase inhibitor)
1.0% *camelia sinensis* extract (antioxidant)
0.5% hyaluronic acid
DAC base cream 2.
1.0% accetoxy-androstenedione (steroidal aromatase inactivator)
1.2% *serenoa serrulata* fruit extract (5-α-reductase inhibitor)
0.5% alpha lipoic acid (antioxidant)
0.5% hyaluronic acid
DAC base cream The composition is typically applied to the respective skin areas 1-2 times per day. Therein, normally 1-5 g of, for example, a cream or 2-5 ml of, for example, a spray are used for each application.

The active ingredients or the composition, respectively, can be present in a suitable container, e.g. a potty, a jar, or a tube.

In one embodiment, the following amounts are applied to the affected skin area:

5-α-reductase inhibitor, e.g. extract exhibiting 5-α-reductase inhibiting function (e.g. *serenoa serrulata* fruit extract): 20 ng/g skin tissue-40 ng/g skin tissue, preferably about 30 ng/g skin tissue steroidal aromatase inhibitor, e.g. brassica campestris extract: 25 ng/g skin tissue-45 ng/g skin tissue, preferably about 30 ng/g skin tissue antioxidant, e.g. alpha lipoic acid or camelia sinensis extract: 25 ng/g skin tissue-40 ng/g skin tissue, preferably about 30 ng/g skin tissue The present application is further illustrated by the following examples, without being limited by these.

EXAMPLES

The following Examples 1 and 2 illustrate the effectiveness of the use according to the invention in the case of spider veins.

The following composition has been used therein:
1.0% acetoxyandrostenedione
0.5% α-lipoic acid
0.5% hyarolonic acid
as active ingredients
in DAC basic cream:
4.0 g glycerolmonostearate
6.0 g cetyl alcohol
7.5 g medium chain triglycerides (neutral oil, miglyol)
25.5 g white vaseline
7.0 g Macrogol-20-glycerolmonostearate
10.0 g propylenglycol
40.0 g purified water.

Example 1

S.H.C., 48 years, female: spider veins at the inner parts of the thighs at knee level on both sides as well as a strong circular accumulation (diameter about 1.5 cm) on the backside of the left thigh slightly above the knee.

After twice-daily treatment for four weeks with the cream according to the invention: the circular accumulation on the backside is already dissolved, only spider veins are visible, which are elongated but continue to become lighter. The treatment is continued as completely without side-effects.

Example 2

E.C., 51 years, female: spider veins at the outer parts of both thighs and at the calves.

After twice-daily treatment with the cream according to the invention over a period of three months: almost no visible spider veins remaining.

The treatment is continued with application once daily as completely without side-effects.

The following Example 3 shows the results of female trial subjects with cellulite. The following cream composition has been used therein once per day (about 1.5 g per afflicted body side; %-indications in weight-%):
0.6% acetoxyandrostenedione
0.5% α-lipoic acid
0.2% hyaloronic acid
as active ingredients
in DAC basic cream:
4.0 g glycerolmonostearate
6.0 g cetyl alcohol
7.5 g medium chain triglycerides (neutral oil, miglyol)
25.5 g white vaseline
7.0 g Macrogol-20-glycerolmonostearate
10.0 g propylenglycol
40.0 g purified water.

Example 3: Observational Study With 50 Female Trial Subjects

The subjects were treated in 5 Swiss health studios. Only subjects having a cellulite expression of score points 2 and 3 of the cellulite evaluation score according to Nürnberger & Müller (Nürnberger F., Müller G.: So-called Cellulite: an invented disease. J. Dermatol. Surg. Oncol. 1978, 4: 221-9) were included.

Nürnberger Score: 0=no orange skin (cellulite)
1=mild expression
2=moderate expression
3=strong expression The study proceeded for 12 weeks. Observation time points 0: prior to treatment/beginning of treatment; further time points for examination after week 4, 8 and 12.

The subjects had an average age of 36 years (19-57 years), were healthy and of normal weight or slightly overweight. Therapy results (after 12 weeks; evaluated according to Nürnberger score):

At the beginning of the therapy:
29 subjects; score 2
21 subjects; score 3

All test persons underwent the 12 week observation period; results after 12 weeks of application:

Out of 29 subjects with moderate expression at the beginning, 20 subjects had no more cellulite (score 0), 9 test persons score 1, mild expression. Out of the 21 score 3 subjects, 8 subjects had score 2 after 12 weeks; 11 score 1; 2 score 0. None of the subjects complained about undesired effects; the cream was perceived as very pleasant and effective. For the maintenance or the further improvement of the results, respectively, the subjects continue the application, namely with the identical cream composition.

Example 4: Double Blind, Three-Arm, Study—Spider Veins, Stretch Marks, Cellulite, Skin-Aging (Evaluated via Skin Tightening)

The following examples exemplify the effect of the composition according to the present invention with regard to spider veins, stretch marks, cellulite, skin-aging (evaluated via skin tightening).

Study plan:
i. Aim of the Study:
1. Circumference thigh (CT), measured 10 cm below the leg joint (best parameter for determining increase in skin tightening (increase in collagen and elastin), and thus indicator for improvement of appearance of skin-aging)
2. Cellulite: Evaluation according to Nürnberger (Scale 1)
3. Tolerability (Scale 2)
4. Observations as to stretch marks and spider veins
Scale 1: Skin appearance according to Nürnberger
Scoring of cellulite according to skin appearance
Score 0:
smooth, no dimples
Score 1:
visible dimples upon pinching, which disappear after pinching (pinching test)
Score 2:
dimples in standing position, no dimples in laying position
Score 3:
dimples visible also in laying position
(Cellulite evaluation score according to Nürnberger & Müller)
Scale 2: Tolerability:
1: optimum: no side-effects or incompatibilities
2: good: maybe a few temporary, mild problems
3: sufficient: slight side-effects and slight problems, respectively, however no reason for interrupting the treatment or termination of the study
4: bad: termination of treatment and termination of study, respectively ii. Inclusion criteria:

15 healthy female trial subjects, aged 20-60 years, cellulite score 2-3 according to Nürnberger (Scale 1). Exclusion/termination criteria were gain of weight/loss of weight (more than 2 kg in the course of the study); incompatibilities and side-effects, respectively.

iii. Duration of the study:

12 weeks iv. Procedure:

In the study, 15 evaluable female trial subjects should be included. Because of the usually high drop-out-rate in cosmetic studies, for the three-arm study that was under medical supervision, three times 7, thus 21, female trial subjects were planned and randomized. 7 female trial subjects were respectively allocated to treatment group A, B, and C.

The treatment groups were as follows:
A. 1.0% acetoxy-androstenedione (steroidal aromatase-inactivator)
0.5% hyaluronic acid (fine distribution in the skin)
DAC basic cream:
    4.0 g glycerolmonostearate
    6.0 g cetyl alcohol
    7.5 g medium chain triglycerides (neutral oil, miglyol)
    25.5 g white Vaseline
    7.0 g macrogol-20-glycerolmonostearate
    10.0 g propyleneglycol
    40.0 g purified water
B. 1.5% brassica campestris (steroidal aromatase-inactivator)
    1.2% serenoa serrulata fruit extract (5-alpha reductase inhibitor)
    1.0% camelia sinensis extract (antioxidant, protection of the cell)
    0.5% hyaluronic acid (fine distribution in the skin)
    DAC basic cream
C. 1.0% acetoxy-androstendione (steroidal aromatase-inactivator)
    1.2% serenoa serrulata fruit extract (5-alpha reductase inhibitor)
    0.5% alpha lipoic acid (antioxidant)
    0.5% hyaluronic acid (fine distribution in the skin)
    DAC basic cream Double-Blind Study For each female trial subject, respectively three dispensers with 100 ml each, containing the randomized treatment, have been prepared. One dispenser was for 4 weeks, 3 dispensers for the whole duration of the study of 12 weeks. The dispensers were only labeled with: "Anti-cellulite cream", and the number of the respective female trial subject. All necessary further information (for instance the detailed composition) have been handed over prior to the start of the study to the medical director, enclosed in so-called "emergency envelopes". All envelopes were returned back end of April 2015 unopened to the organizer of the study. This means that all conditions of a so-called double-blind study have been met.

As the study was a double-blind study, only the organizer was then able to unblind and evaluate the study results.

The results of the study were as follows:

v. Results of the Study

Treatment Group A
The overall result is as follows:
thigh right, total increase: +1 cm
average increase: +0.25 cm
cellulite score total: −1
average score: −0.25

Three female trial subjects did not show any improvement with regard to spider veins and stretch marks.

Treatment Group B
The overall result was as follows:
thigh right, total decrease: −24 cm
average decrease: −4 cm
cellulite score total: −12
average score: −1.7

Treatment Group C
The overall result is as follows:
thigh right, total decrease: −7 cm
average decrease: −1.75 cm
cellulite score total: −5.5
average score: −1.4

The positive effect (improvement) with regard to stretch marks and spider veins was comparably good in female trial subjects of treatment groups B and C.

vi. Conclusion

Treatment groups B and C were superior to treatment group A (which was a treatment with aromatase-inactivator+hyaluronic acid only), in particular with respect to:
decreasing score of cellulite;
improvement of appearance of spider veins;
improvement of appearance of stretch marks; and
improvement of skin tightening.

Treatment group B (treatment with specifically enriched (active) plant extracts) showed the best results with regard to decrease of circumference of thigh (skin tightening) and with regard to decrease of the cellulite score.

With regard to influencing of spider veins and stretch marks, treatment groups B+C were comparably good.

Treatment group A did not show any positive effect with regard to spider veins and stretch marks.

The results of this study demonstrate a synergistic effect between the steroidal aromatase-inactivator and the 5-alpha reductase inhibitor. That is the results of this study demonstrate a surprising and unexpected benefit which is greater than the additive effect of either component individually.

This effect was particularly observed in composition B, which utilized a plant-based steroidal aromatase-inactivator.

The invention claimed is:

1. A method for improving a general condition and appearance of skin, the method comprising treating a patient for cosmetic purposes with a composition comprising the following active ingredients:
an aromatase inhibitor and a 5-α-reductase inhibitor,
an antioxidant, and
hyaluronic acid;
wherein
the aromatase inhibitor is a steroidal aromatase-inactivator; the 5-α-reductase inhibitor is selected from the group consisting of an extract from the fruit of saw palmetto (Serenoa repens, syn. Sabal serrulata), an extract from the root of stinging nettle (Urtica dioica), a bark extract of Pygeum africanium, and an extract from pumpkin seed (Cucurbita pepo seed);
the antioxidant is an α-lipoic acid or a green tea extract, wherein the green tea extract contains polyphenols;
the aromatase inhibitor is present in the composition in a concentration from 0.25 weight-% to 1.8 weight-%;
the 5-α-reductase inhibitor is present in the composition in a concentration from 0.5 weight-% to 5 weight-%; and the antioxidant is present in the composition in a concentration from 0.2 weight-% to 2.5 weight-%;
wherein the composition is administered topically to the skin;
and wherein the method comprises:
a) administering 20 ng/g skin tissue to 40 ng/g skin tissue of the 5-α-reductase inhibitor to the patient,
b) administering 25 ng/g skin tissue to 45 ng/g skin tissue of the steroidal aromatase inhibitor to the patient, or
c) administering 25 ng/g skin tissue to 40 ng/g skin tissue of the antioxidant to the patient.

2. The method according to claim 1, wherein the aromatase inhibitor is selected from the group consisting of 4-hydroxyandrostenedione, Exemestane, 4-acetoxyandrostenedione, 5-α-androst-3-ene-17-one and 3-α,4-α-epoxy-5-α-androstane-17-one.

3. The method according to claim 1, wherein the aromatase inhibitor is a plant-based aromatase inhibitor.

4. The method according to claim 1, wherein the aromatase inhibitor has a mean inhibitory concentration IC(50) in a range from 0.2 nM to 500 nM.

5. The method according to claim 1, wherein the 5-α-reductase inhibitor has a mean inhibitory concentration IC(50) in a range from 5 nM to 500 nM.

6. The method according to claim 1, wherein the composition comprises (i) 4-acetoxyandrostenedione or a plant-based-aromatase inhibitor, (ii) saw palmetto extract, (iii) α-lipoic acid or green tea extract containing polyphenols, and (iv) hyaluronic acid.

7. The method according to claim 1, wherein the method comprises administering 20 ng/g skin tissue to 40 ng/g skin tissue of the 5-α-reductase inhibitor to the patient.

8. The method according to claim 1, wherein the method comprises administering 25 ng/g skin tissue to 45 ng/g skin tissue of the steroidal aromatase inhibitor to the patient.

9. The method according to claim 1, wherein the method comprises administering 25 ng/g skin tissue to 40 ng/g skin tissue of the antioxidant to the patient.

10. The method according to claim 1, wherein the method comprises administering 20 ng/g skin tissue to 40 ng/g skin tissue of the 5-α-reductase inhibitor to the patient; administering 25 ng/g skin tissue to 45 ng/g skin tissue of the steroidal aromatase inhibitor to the patient; and administering 25 ng/g skin tissue to 40 ng/g skin tissue of the antioxidant to the patient.

11. The method according to claim 1, wherein:
the aromatase inhibitor is present in the composition in a concentration from 0.5 weight-% to 1.8 weight-%.

12. The method according to claim 1, wherein:
the 5-α-reductase inhibitor is present in the composition in a concentration from 0.8 weight-% to 2.0 weight-%.

13. The method according to claim 1, wherein:
the antioxidant is present in the composition in a concentration from 0.2 weight-% to 1.0 weight-%.

* * * * *